United States Patent [19]

Siegemund et al.

[11] 3,980,714
[45] Sept. 14, 1976

[54] 2,2,2-TRIFLUORO-1-CHLOROETHYL ETHERS AND PROCESS FOR PREPARING THEM

[75] Inventors: Günther Siegemund, Hofheim, Taunus; Roman Muschaweck, Frankfurt am Main, both of Germany

[73] Assignee: Hoechst Aktiengesellschaft, Frankfurt am Main, Germany

[22] Filed: Aug. 8, 1974

[21] Appl. No.: 495,898

[30] Foreign Application Priority Data
Aug. 10, 1973 Germany............................ 2340561

[52] U.S. Cl. ............................ 260/614 F; 424/342; 424/339; 260/611 A; 260/615 A; 260/615 F; 260/615 BF
[51] Int. Cl.².......................................... C07C 43/12
[58] Field of Search................................. 260/614 F

[56] References Cited
UNITED STATES PATENTS

| | | | |
|---|---|---|---|
| 3,535,388 | 10/1970 | Terrell............................ | 260/614 F |
| 3,535,425 | 10/1970 | Terrell........................ | 260/614 F X |
| 3,764,706 | 10/1973 | Terrell............................ | 260/614 F |

OTHER PUBLICATIONS

Terrell et al., J. Med Chem., 14, pp. 517–519 (1971).
Siegemund, Chem. Abst. 80, 3031y, 1974.
Chem. Ber. (1973) 106(9) pp. 2960–2968.

*Primary Examiner*—Howard T. Mars
*Attorney, Agent, or Firm*—Curtis, Morris & Safford

[57] ABSTRACT

2,2,2-trifluoro-1-chloroethyl ethers, useful as inhalation anesthetics, of the formula

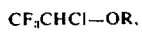

$$CF_3CHCl-OR.$$

wherein R is alkyl, alkylphenyl, haloalkyl, or alkyloxyhaloalkyl, and methods for making and using the same.

3 Claims, No Drawings

2,2,2-TRIFLUORO-1-CHLOROETHYL ETHERS AND PROCESS FOR PREPARING THEM

The present invention relates to 2,2,2-trifluoro-1-chloroethyl ethers of the general formula I $$CF_3CHCl—OR \qquad (I)$$

in which R represents a straight chain or branched alkyl radical of 1 to 8 carbon atoms which may be substituted by phenyl, the radical $-CH_2CH_{3-n}X_n$, $n$ being 1 to 3 and X being fluorine and/or chlorine, or the radical $-Y-OCHCl-CF_3$, X representing a straight chain or branched alkyl radical of 2 to 4 carbon atoms.

The invention furthermore relates to a process for preparing the above-specified 2,2,2-trifluoro-1-chloroethyl ethers, which comprises a. reacting a fluoral-semi-acetal of the formula II $$\begin{array}{c} CF_3CH—OR \\ | \\ OH \end{array} \qquad (II)$$

in which R has the meaning given for formula I, with a chlorinating agent, or b. reacting a 2,2-difluorovinyl ether of the formula III $$CF_2=CH—OR \qquad (III)$$

in which R has the meaning given for formula I, with hydrogen fluoride and hexachloromelamine, or c. fluorinating compounds of the formula IV $$CF_nCl_{3-n}CHCl—OR \qquad (IV)$$

in which R has the meaning given above and $n$ is 0 to 2.

The invention also relates to inhalation anesthetics which contain a compound of the formula I, the use of compounds of the formula I as inhalation anesthetics and to a method of anesthetising living beings with the use of compounds of the formula I.

The reaction according to method (a) is carried out with a chlorinating agent, for example phosphorus pentachloride, thionyl chloride, titanium tetrachloride, triphenylphosphine dichloride or the compound 2,2,2-trichloro-benzo-1,3,2-dioxaphospholine of the formula

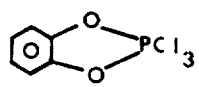

optionally in the presence of a tertiary base, for example triethylamine or pyridine and/or a solvent in a wide temperature range of from −10° to +100° C or to the boiling point of the reaction mixture. The preferred reaction temperature is in the range of from 0° to +25° C.

As a solvent, there may be used methylene chloride, tetrahydrofurane, diethyl ether, di-isopropyl ether, di-n-butyl ether, or di-n-hexyl ether. It is preferred to work in diethyl ether or di-n-butyl ether.

The compounds of the invention are isolated in known manner from the reaction product and purified.

If $PCl_5$ is used, the reaction of the invention proceeds according to the reaction scheme (1):

$$CF_3CH(OH)—OR + PCl_5 \longrightarrow CF_3CHCl—OR + POCl_3 + HCl \qquad (1)$$

or, if R is $$\begin{array}{c} -Y-O-CH-CF_3 \\ | \\ OH \end{array}$$

Y having the meaning given above:

$$CF_3-CH(OH)-O-Y-O-CH(OH)-CF_3 + 2 PCl_5 \longrightarrow CF_3CHCl-O-Y-O-CHCl-CF_3 + 2POCl_3 + 2 HCl$$

The process is preferably carried out without addition of tertiary bases. As a solubilizer, $POCl_3$ may suitably be added. In the chlorination with the acid chloride of the formula

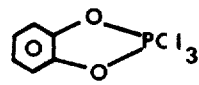

the process can be carried out without addition of bases in suitable ethers, for example in di-n-butyl ether. The reaction with $SOCl_2$ is effected in the presence of a tertiary base, for example pyridine or triethylamine, and an ether as solvent.

In these reactions it is surprising that, despite the known dissociation equilibrium $$CF_3CH(OH)—OR \rightleftarrows CF_3CHO + ROH$$

in solution, the chlorination of the alcohol ROH takes place relatively slowly, so that the 2,2,2-trifluoro-1-chloroethyl ethers of the invention are obtained in good yields.

The starting compounds used in method (a) may be prepared by addition of the corresponding alcohols onto fluoral.

In method (b), a 2,2-difluoro-vinyl ether is treated in a temperature range of from −30° C to room temperature, preferably at 0° C, optionally in an ether as solvent, in the presence of hexachloromelamine with hydrogen fluoride in excess. 2 moles of hexachloromelamine and 8 moles of HF are preferably used per mole of starting compound.

The compounds of the invention are isolated in known manner from the reaction product and purified.

The reaction takes place according to the reaction scheme (2):

$$CF_2=CH—OR \xrightarrow[\text{hexachloromelamine}]{HF} CF_3CHCl—OR \qquad (2)$$

The starting compound $CF_2=CH—OR$ can be prepared analogously to the process described in U.S. Pat. No. 2,870,219. From the compound $CClF_2CHO$, which corresponds to chloral and can be synthesized by hydrogenation of the corresponding acid chloride C ClF₂COCl over palladium, the corresponding semiacetal C ClF₂CH(OH)—OR can be prepared by the addition of an alcohol. By the reaction with SOCl₂, this compound is reacted to the compound C ClF₂—CHCl—OR from which 1 mole of Cl₂ is split off with zinc in methanol.

The reaction according to method (c) proceeds according to the reaction scheme (3):

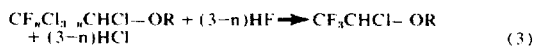
(3)

The compound of the formula IV is passed, for example in the gaseous state with about the 1 to 1.5 fold stoichiometrical amount of hydrogen fluoride at a temperature of 150°–350° C over chromium oxyfluoride as the catalyst. The reaction products in gaseous form are dissolved in water in order to separate the hydrohalic acids. The organic phase is treated with a bicarbonate solution, dried in the usual manner and subjected to fractional distillation. The starting compounds of the formula IV may be prepared according to the process described in U.S. Pat. No. 2,870,219 or in a manner analogous to this process.

The 2,2,2-trifluoro-1-chloroethyl-ethers of the invention are colorless, easily mobile liquids with a faint agreeable odor. They are completely miscible with organic liquids and have a good dissolving power, especially for fluorinated olefins and other fluorine-containing organic compounds.

The physical properties and spectroscopic data of the compounds of the invention CF₃CHCl—OCH₃ and CF₃CHCl—OC₂H₅ are compiled in Table 1.

Table 1

| Compound | CF₃CHCl—OCH₃ | CF₃CHCl—OC₂H₅ |
|---|---|---|
| Molecular weight | 148.5 | 162.5 |
| Boiling point (°C) | 68/759 mm | 85.5/753 mm |
| Refraction index | n_D²⁵ 1.3297 | n_D²⁵ 1.3422 |
| ¹H-NMR spectrum | δ= 3.58 ppm (s, CH₃) | δ= 1.30 ppm (t, CH₃) |
|  | δ= 5.50 ppm (q,J=5Hz,CH) | δ= 3.87 ppm (m,J=7Hz,CH₂ |
|  |  | δ= 5.66 ppm (q,J=5Hz,CH) |

When added to the breathing air of living beings, the 2,2,2-trifluoro-1-chloroethyl ethers of the invention have an anesthetising action and may, therefore, be used as inhalation anesthetics. They are difficult to ignite under normal conditions and stable to the so-called breathing lime which is usually employed in anesthesia apparatuses for the absorption of CO₂ from the breathing air and which consists, for example of a mixture of Ca(OH)₂ and Ba(OH)₂. Furthermore, they do not separate hydrogen halides at room temperature, as is the case, for example, with 1,1-difluoro-2,2-dichloroethyl-methyl ether.

Their great stability is surprising, since even known compounds of analogous constitution such as CCl₃CHCl—OCH₃ and CCl₃CHF—OCH₃ are very reactive α-halogen ethers which are not stable to acids and to bases.

The compounds of the invention may also be used as intermediate products for the preparation of other anesthetics.

In particular, the easily volatile lower homologues CF₃CHCl—OCH₃ and CF₃CHCl—OC₂H₅ and the derivatives of the last-mentioned compound which are fluorinated twice or thrice in the 2-position of the ethyl group have a very good anesthetising action on anesthetisable living beings.

Owing to their relatively low boiling point, the compounds of the invention can be admixed in simple and controllable manner to breathing mixtures which secure the maintenance of life during anesthesia by a sufficient concentration of oxygen.

The action of the ethers of the invention as inhalation anesthetics is proved by the results of a pharmacological test in which the compounds CF₃CHCl—OCH₃ and CF₃CHCl—OC₂H₅ have been compared with the commercial 1,1-difluoro-2,2-dichloroethylmethyl ether. With regard to the action of the ethers of the invention, it is remarkable that, besides a relatively low excitation, the period of time until awakening of the animals is short in comparison to that of the comparative substance.

The pharmacological test was carried out by exposing groups of 4 mice each in a closed glass bell of a capacity of 26 liters to anesthesia mixtures produced by evaporation of the claimed (2,2,2-trifluoro-1-chloroethyl)-alkyl ethers of the invention or of the comparative compound in various quantities. The animals were left in the gas room each time for a period of 10 minutes. The course of anesthesia and the awakening of the animals were observed.

In the following Table 2, the time $t_I$ until the beginning of the tolerance stage and the time $t_{II}$ until the awakening of the mice is indicated in dependence on the concentration of the anesthetic (ml of evaporated liquid per 26 liters of air).

Table 2

| Substance | 2.0 ml/26 Ltr. | | 2.5 ml/26 Ltr. | | 5.0 ml/26 Ltr. | |
|---|---|---|---|---|---|---|
|  | $t_I$ | $t_{II}$ | $t_I$ | $t_{II}$ | $t_I$ | $t_{II}$ |
| CF₃CHCl—OCH₃ | 3'25'' | 5'25'' | 2'55'' | 6'15'' | 2'10'' | 9'15'' |
| CF₃CHCl—OC₂H₅ | 6'05'' | 5'15'' | 3'50'' | 5'40'' | 2'30'' | 14' |
| CHCl₂CF₂OCH₃ (comparative substance) |  |  | 3'30'' | 9'20'' | 1'30'' | 14'40'' |

The comparison of the test results shows that the ethers of the invention are distinguished in particular by a more favorable shorter recovery time ($t_{II}$). Thereby, the risk of side effects caused by the anoxia occurring during anesthesia, in particular of the cardiac muscle and of the parenchymatous organs, especially of the liver is considerably reduced. Compared to the standard substances, the novel compounds of the invention have advantageous properties when used as inhalation anesthetics with anesthetisable living beings.

The ethers of the invention may also be used together with other inhalation anesthetics, for example nitrous oxide or diethyl ether, furthermore with other anesthetic or therapeutic auxiliary agents, for example muscle relaxants, barbiturates and plasma expanders, as is often required in modern combination anesthesia.

The following Examples illustrate the invention.

EXAMPLE 1

100 ml of phosphorus oxychloride were introduced into a four-necked flask having a capacity of 2 liters and provided with stirrer, dropping funnel, thermometer, Anschütz head piece with gas drain pipe over a deep temperature condenser and opening for the addition of solids. 1370 g (6.6 moles) of phosphorus pentachloride were added portionwise at a temperature of from 0° to 10° C, while at the same time 780 g (6,6 moles) of fluoralmethyl-semiacetal were added dropwise. The hydrogen chloride that was forming was absorbed in water and determined by titration (6,24 moles). After 7 hours, the reaction was completed, the evolution of HCl had ceased and the solution had become clear.

(2,2,2-trifluoro-1-chloroethyl)-methyl ether was subsequently obtained from the reaction mixture by fractional distillation.

Yield: 719 g = 84 % of the theory.
$CF_3CHCl—OCH_3$, M.W. 148.5
Analysis: Calc.: C, 24.2 %; H, 2.7 %; F, 38.4 %; Cl, 23.9 %. Found: C, 24.0 %; H, 2.6 %; F, 38.3 %; Cl, 22.7 %.

EXAMPLE 2

By chlorination of the corresponding fluoral-semiacetal with phosphorus pentachloride in a manner analogous to that described in Example 1, (2,2,2-trifluoro-1-chloroethyl)-ethyl ether $CF_3CHCl—O—C_2H_5$ was obtained.

Yield: 71% of the theory.
Analysis: Calc.: C, 29.6 %; H, 3.7 %; F, 35.1 %; Cl, 21.8 %. Found: C, 29.6 %; H, 3.9 %; F, 35.4 %; Cl, 21.5 %.

The (2,2,2-trifluoro-1-chloroethyl)-alkyl ethers indicated in Table 3 were likewise obtained in the same manner.

Table 3

|  | Boiling point °C | Yield (%) |
|---|---|---|
| $CF_3CHCl—O—CH(CH_3)_2$ | 99–100/755 mm | 28 |
| $CF_3CHCl—O—CH_2CH_2Cl$ | 82.5/99 mm | 55 |
| $CF_3CHCl—O—(CH_2)_3CH_3$ | 58/1.5 mm | 78 |
| $CF_3CHCl—O—CH_2CH_2C_6H_5$ | 68.5/1.2 mm | 70.5 |
| $CF_3CHCl—O—CH_2$ <br> \| <br> $CF_3CHCl—O—CH_2$ | 96/31 mm | 40 |
| $CF_3CHCl—O—CH(CH_3)$ <br> \| <br> $CF_3CHCl—O—CH_2$ | 46/1.3 mm | 55 |
| $CF_3CHCl—O—CH_2CF_3$ | 77/754 mm | 55 |

EXAMPLE 3

250 g (1.1 mole) of 2,2,2-trichloro-benzo-1,3,2-dioxaphospholine were dissolved in 300 ml of di-n-butyl ether in a four-necked flask having a capacity of 1 liter and provided with dropping funnel, thermometer and reflux condenser with connected HCl absorption. 158 g (1 mole) of fluoral-isopropylsemiacetal were added dropwise at a temperature of +5° C. After combination of the components, the mixture was slowly heated to 62° C, during which time HCl separated. The isolation of $CF_3CHClOCH(CH_3)_2$ was subsequently carried out by fractional distillation through a packed column. 117.5 g (67 % of the theory) of $CF_3CHClOCH—(CH_3)_2$ were obtained. Boiling point: 106° C/765 mm.

$CF_3CHClOCH(CH_3)_2$, M.W. 176.5
Analysis: Calc.: C, 34.0 %; H, 4.5 %; F, 32.3 %; Cl, 20.1 %. Found: C, 35.2 %; H, 4.9 %; F, 31.1 %; Cl, 19.7 %.

EXAMPLE 4

285 g of 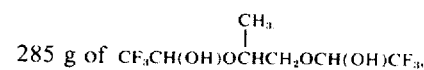

dissolved in 250 ml of anhydrous diethyl ether, were added dropwise to a mixture of 238 g (2 moles) of $SOCl_2$ and 158 g (2 moles) of pyridine in 750 ml of anhydrous diethyl ether at an internal temperature of 0° C, which mixture had been placed in a stirring flask provided with stirrer, reflux condenser, thermometer and dropping funnel. A white precipitate of pyridine hydrochloride formed. After standing overnight, 350 ml of water were added, the phases were separated and the ether solution was shaken several times with water, then with bicarbonate solution until the reaction was neutral. The organic phase was dried with $MgSO_4$. After removal of the ether by distillation, the residue was distilled under reduced pressure. 169 g (55% of the theory) of

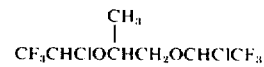

were obtained. Boiling point: 46° C/1.3 mm.
$CF_3CHClOCH(CH_3)CH_2OCHClCF_3$, M.W. 309
Analysis: Calc.: C, 27.2 %; H, 2.6 %; F, 36.9 %; Cl, 23.0%. Found: C, 27.3 %; H, 2.7 %; F, 36.9 %; Cl, 22.6 %.

In analogous manner, there were obtained:
$CF_3CHClOCH_2CH_2Cl$, M.W. 197 B.p. 141° C/755 mm, yield: 45 %.
$CF_3CHClOC_2H_5$, M.W. 162.5 B.p. 85° C/754 mm, yield: 43 %.

EXAMPLE 5

92 g (2 moles) of absolute ethanol were placed into a stirring flask having a capacity of 1 liter and provided with stirrer, thermometer, dropping funnel and $CaCl_2$ tube with connected $H_2O$-absorption vessel for HCl, and 190 g (1 mole) of $TiCl_4$ were added dropwise at 20° C. The mixture was stirred for 1 hour at room temperature. Then, likewise at room temperature, 144 g (1 mole) of fluoral-ethyl-semiacetal were added. After standing overnight, the reaction product was poured on ice, the organic phase was separated, neutralized with sodium carbonate and dried with sodium sulfate. Upon fractional distillation, 90 g (55% yield) of $CF_3CHClOC_2H_5$ were obtained. Boiling point: 86° C/761 mm, $n_D^{20} = 1.3449$.

$CF_3CHClOC_2H_5$, M.W. 162.5
Analysis: Calc.: C, 29.6 %; H, 3.7 %; F, 35.1 %; Cl, 21.8 %. Found: C, 29.8 %; H, 3.7 %; F, 33.9 %; Cl, 21.2 %.

We claim:

1. A 2,2,2-trifluoro-1-chloroethyl ether of the formula $$CF_3CHCl-OR.$$

wherein R is methyl or ethyl.

2. A compound as in claim 1 which is $$CF_3CHClOCH_3.$$

3. A compound as in claim 1 which is $$CF_3CHClOC_2H_5.$$

* * * * *